(12) United States Patent
Reid et al.

(10) Patent No.: US 9,044,011 B2
(45) Date of Patent: Jun. 2, 2015

(54) PESTICIDAL COMPOSITIONS

(75) Inventors: Byron Reid, Raleigh, NC (US); Johan Kijlstra, Odenthal (DE); Frank Rosenfeldt, Langenfeld (DE); Guenther Nentwig, Leverkusen (DE); Volker Gutsmann, Langenfeld (DE); Rainer Sonneck, Leverkusen (DE)

(73) Assignee: Bayer Cropsciece LP, Research Triangle Park, NC (US)

( * ) Notice: Subject to any disclaimer, the term of this patent is extended or adjusted under 35 U.S.C. 154(b) by 30 days.

(21) Appl. No.: 13/978,141

(22) PCT Filed: May 25, 2011

(86) PCT No.: PCT/US2011/037901
§ 371 (c)(1),
(2), (4) Date: Sep. 3, 2013

(87) PCT Pub. No.: WO2012/003060
PCT Pub. Date: Jan. 5, 2012

(65) Prior Publication Data
US 2013/0338223 A1 Dec. 19, 2013

Related U.S. Application Data

(60) Provisional application No. 61/361,013, filed on Jul. 2, 2010.

(51) Int. Cl.
*A01N 25/04* (2006.01)
*A01N 25/24* (2006.01)
*A01N 25/10* (2006.01)

(52) U.S. Cl.
CPC ............... *A01N 25/04* (2013.01); *A01N 25/24* (2013.01); *A01N 25/10* (2013.01)

(58) Field of Classification Search
None
See application file for complete search history.

(56) References Cited

U.S. PATENT DOCUMENTS

| | | | |
|---|---|---|---|
| 4,303,642 A | 12/1981 | Kangas | |
| 5,023,247 A | 6/1991 | Boulanger et al. | |
| 6,638,994 B2 * | 10/2003 | Crooks et al. | 523/122 |
| 2006/0003014 A1 * | 1/2006 | Jadhav et al. | 424/490 |
| 2008/0171658 A1 | 7/2008 | Dyllick-Brenzinger et al. | |
| 2008/0286226 A1 | 11/2008 | Toreld, III et al. | |
| 2009/0317433 A1 | 12/2009 | Finch et al. | |
| 2011/0071228 A1 | 3/2011 | Kijlstra et al. | |

FOREIGN PATENT DOCUMENTS

| | | |
|---|---|---|
| DE | 2804563 A1 | 8/1979 |
| EP | 0 862 856 A1 | 9/1998 |
| EP | 0862856 A1 | 9/1998 |
| WO | 94/10979 A1 | 5/1994 |
| WO | 9410979 A1 | 5/1994 |
| WO | 03/034823 A1 | 5/2003 |
| WO | 03034823 A1 | 5/2003 |
| WO | 2009141109 A2 | 11/2009 |

OTHER PUBLICATIONS

European Search Report of EP Application No. 11 801 308.5.
International Search Report for PCT/US2011/037901 Mailed Aug. 30, 2011.
Written Opinion for PCT/US2011/037901 Completed Aug. 30, 2011.
Jorgenson "Formulation Effects and the Off-Target Transport of Pyrethroid Insecticides From Urban Hard Surfaces", Environ. Sci. Technol. (2010) vol. 44, pp. 4951-4957.
Battany et al. "Development of a Portable Field Rainfall Simulator for Use in Hillside Vineyard Runoff and Erosion Studies", Hydrological Process, vol. 14 (2000) pp. 1119-1129.

* cited by examiner

*Primary Examiner* — Kyle Purdy
(74) *Attorney, Agent, or Firm* — Miles & Stockbridge P.C.

(57) ABSTRACT

The present invention relates to compositions for the control of pests, to processes for their preparation, and to methods of treating surfaces with such formulations for the sustained weather-resistant control of pests. The composition includes a pesticide and an aqueous polymer dispersion.

11 Claims, 1 Drawing Sheet

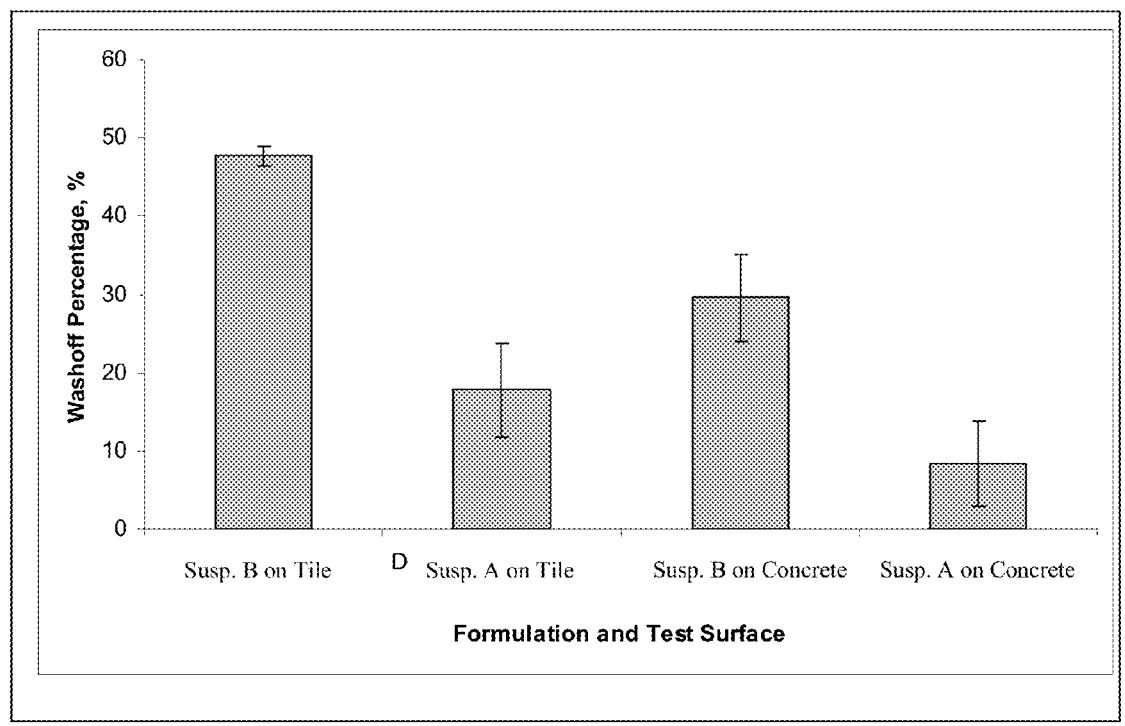

PESTICIDAL COMPOSITIONS

CROSS REFERENCE TO RELATED APPLICATIONS

This application is a §371 National Stage Application of PCT/US2011/037901, filed May 25, 2011, which claims priority to U.S. Provisional Application No. 61/361,013, filed Jul. 2, 2010.

BACKGROUND OF THE INVENTION

1. Field of the Invention

The present invention relates to compositions for the control of pests, methods of making such compositions, and methods of controlling pests with such compositions.

2. Description of Related Art

The control of pests, in particular arthropods, inside and outside of buildings and houses is necessary for a variety of reasons, for example, to prevent disease transmission, to maintain hygienic standards, and to avoid structural destabilization of structures. The most frequently used control method is the application of pesticidal active substances in aqueous spray or atomizing solutions. Independently of the active substance used, the activity of the spray coating greatly depends on the physicochemical properties of the sprayed surface and the environmental effects surrounding the treated area. For example, the coating's activity duration may be reduced on porous, and in particular alkaline porous, surfaces such as concrete, render, ashlar/brick, timber (treated and untreated), ceramic, straw or thatch, chalky, limy, gypsiferous, cement-containing and loamy surfaces. Additionally, the environmental effects of temperature, UV, and rain, can adversely affect the activity of the active substances employed.

In many conventional formulations, exposure to water (rain, snow, sprinkler systems, irrigation, etc.) can wash away the active substances, resulting in environmental degradation and a need to frequently reapply the formulations. Reapplication in turn results in increased exposure of the user, the inhabitants of the structure, domestic animals, and the environment to the formulations. In particular, the washed-off active substances enter the environment and water systems, potentially affecting areas where pesticide residues represent an ecological threat and/or are undesirable.

A need exists for improved pesticidal formulations that provide longer-term protection by reducing the environmental degradation and wash-off of the active substances from the treated surface without negatively affecting the efficacy of the active substance.

SUMMARY

The present invention in aspects and embodiments addresses these various needs and problems by providing a pesticidal composition comprising a pesticide, and an aqueous polymer dispersion. The aqueous polymer dispersion provides weather resistance to the pesticidal composition after application. Embodiments include aqueous suspension concentrates, spray mixtures, aqueous polymer dispersions, methods for making such compositions, and methods of treating surfaces with such compositions. Spray mixtures that may be employed in accordance with the invention may be prepared by diluting a concentrate in water or by mixing various pre-existing solutions directly before spraying (tank-mix application). Compositions may also be ready-to-use (RTU) formulations.

The compositions are preferably solvent-free, simple to handle, simple to produce, and readily re-dispersible in water with only very little sedimentation of the spray mixture. The compositions are also advantageously and surprisingly weather resistant. In addition, the efficacy of the active ingredient may be improved by the addition of the aqueous polymer dispersion.

These and other improvements are accomplished by the compositions and methods described herein.

BRIEF DESCRIPTION OF THE DRAWINGS

FIG. 1 is a graphical representation illustrating the percentage wash-off of a formulation according to the instant disclosure and a conventional formulation.

DETAILED DESCRIPTION OF A PREFERRED EMBODIMENT

This disclosure is not limited to the particular embodiments described herein, and some components and methods may be varied by one of ordinary skill, based on this disclosure.

Pesticidal compositions of the invention provide superior pesticidal affect while maintaining these effects despite environmental conditions, in particular exposure to weather and rain. The improved weather-proof/weather-resistant compositions exhibit a surprising adhesion or fastness to the treated surface, minimizing the wash-away of the composition and maximizing the treatment's effective duration. The polymer also protects the active substance from environmental degradation by, for example, weather conditions and/or application surface materials.

U.S. Provisional Patent Application No. 61/172,265 (filed Apr. 24, 2009) and PCT Application WO 2009/141109 (published Nov. 26, 2009), which are related to the instant application, are herein incorporated by reference in their entirety.

In this specification and the claims that follow, singular forms such as "a," "an," and "the" include plural forms unless the content clearly dictates otherwise. All ranges disclosed herein include, unless specifically indicated, all endpoints and intermediate values. In addition, optional" or "optionally" refer, for example, to instances in which subsequently described circumstance may or may not occur, and include instances in which the circumstance occurs and instances in which the circumstance does not occur. Also, the terms "one or more" and "at least one" refer, for example, to instances in which one of the subsequently described circumstances occurs, and to instances in which more than one of the subsequently described circumstances occurs.

Active Substances.

The formulations include one or more active substances, such as a pesticide or an insecticide, that may be used successfully for destroying and/or controlling harmful and/or nuisance arthropods, in particular arachnids, sucking insects, biting insects, and insects from the orders Diptera, Dictyoptera, and Hymenoptera.

Target arachnids may include mites (for example *Sarcoptes scabiei, Dermatophagoides pteronyssinus, Dermatophagoides farinae, Dermanyssus gallinae, Acarus siro*), and ticks (for example *Ixodes ricinus, Ixodes scapularis, Argas reflexus, Ornithodorus moubata, Rhipicephalus (Boophilus) microplus, Amblyomma hebraeum*, and *Rhipicephalus sanguineus*).

Target sucking insects may include mosquitoes (for example *Aedes aegypti, Aedes vexans, Culex quinquefasciatus, Culex tarsalis, Anopheles albimanus, Anopheles*

*stephensi, Mansonia titillans*), moth gnats (for example *Phlebotomus papatasii*), gnats (for example *Culicoides furens*), buffalo gnats (for example *Simulium damnosum*), stinging flies (for example *Stomoxys calcitrans*), tsetse flies (for example *Glossina morsitans morsitans*), horse flies (for example *Tabanus nigrovittatus, Haematopota pluvialis, Chrysops caecutiens*), true flies (for example *Musca domestica, Musca autumnalis, Musca vetustissima, Fannia canicularis*), flesh flies (for example *Sarcophaga carnaria*), myiasis-causing flies (for example *Lucilia cuprina, Chrysomyia chloropyga, Hypoderma bovis, Hypoderma lineatum, Dermatobia hominis, Oestrus ovis, Gasterophilus intestinalis, Cochliomyia hominivorax*), bugs (for example *Cimex lectularius, Rhodnius prolixus, Triatoma infestans*), lice (for example *Pediculus humanis, Haematopinus suis, Damalina ovis*), fleas (for example *Pulex irritans, Xenopsylla cheopis, Ctenocephalides canis, Ctenocephalides felis*), and sand fleas (*Tunga penetrans*).

Target biting insects may include cockroaches (for example *Blattella germanica, Periplaneta americana, Blatta orientalis, Supella longipalpa*), beetles (for example *Sitophilus granarius, Tenebrio molitor, Dermestes lardarius, Stegobium paniceum, Anobium punctatum, Hylotrupes bajulus*), termites (for example *Reticulitermes lucifugus*), ants (for example *Lasius niger, Monomorium pharaonis*), wasps (for example *Vespula germanica*), and larvae of moths (for example *Ephestia elutella, Ephestia cautella, Plodia interpunctella, Hofmannophila pseudospretella, Tineola bisselliella, Tinea pellionella, Trichophaga tapetzella*).

The compositions may contain any suitable active substance effective against the desired target pest. Exemplary active substances may include one or more of those selected from the group of: pyrethroids, pyrazoles, neonicotinoids, diamides (anthranilamides, benzenedicarboxamides), carbamates, METI (mitochondrial energy transfer inhibitors (respiratory chain complex I-III), botanical insecticides, and inorganic insecticides.

In particular, the compositions may contain at least one pesticide selected from the group of: beta-cyfluthrin, cyfluthrin, cypermethrin, alpha-cypermethrin, deltamethrin, bifenthrin, flumethrin, permethrin, lambda-cyhalothrin, gamma-cyhalothrin, metofluthrin, etofenprox, transfluthrin, pyrethrum, indoxacarb, carbaryl, fipronil, metaflumizone, azadirachtin, flubendiamide, chloranthraniliprole, boric acid, borax, imidacloprid, clothianidin, dinotefuran and acetamiprid, fenpyroximate and tolfenpyrad, and spinosad.

In particular, pyrethroids are suitable pesticides for the purposes of the instant disclosure. For example, pyrethroids such as deltamethrin ($C_{22}H_{19}Br_2NO_3$) and beta-cyfluthrin ($C22H_{18}Cl_2FNO_3$) are suitable pesticides. Deltamethrin, (S)-Cyano(3-phenoxyphenyl)methyl (1R,3R)-3-(2,2-dibromoethenyl)-2,2-dimethylcyclopropanecarboxylate, has the following structural formula (I)

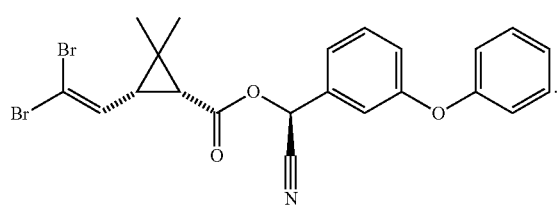

(I)

Beta-cyfluthrin, cyano(4-fluoro-3-phenoxyphenyl)methyl 3-(2,2-dichloroethenyl)-2,2-dimethylcyclopropanecarboxylate, has the following structural formula (II)

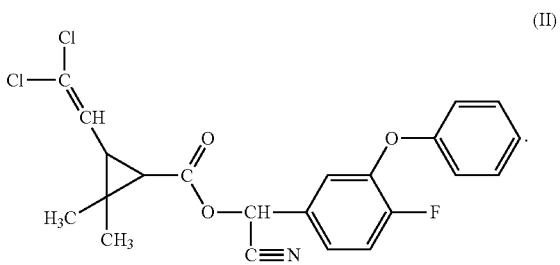 [SMILES: CC1(C)C(C=C(Cl)Cl)C1C(=O)OC(C#N)c1ccc(F)c(Oc2ccccc2)c1]

(II)

In addition to the above-mentioned pesticides, the compositions may contain further pesticidal active substances, for example, substances selected from alanycarb, aldicarb, aldoxycarb, allyxycarb, aminocarb, bendiocarb, benfuracarb, bufencarb, butacarb, butocarboxim, butoxycarboxim, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate, acephate, azamethiphos, azinphos(-methyl, -ethyl), bromophos-ethyl, bromfenvinfos(-methyl), butathiofos, cadusafos, carbophenothion, chlorethoxyfos, chlorfenvinphos, chlormephos, chlorpyrifos(-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion(-methyl/-ethyl), phenthoate, phorate, phosalone, phosmet, phosphamidon, phosphocarb, phoxim, pirimiphos(-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, DDT, nitenpyram, nithiazine, thiacloprid, thiamethoxam, nicotine, bensultap, cartap, spinosad, camphechlor, chlordane, endosulfan, gamma-HCH, HCH, heptachlor, lindane, methoxychlor, acetoprole, ethiprole, pyrafluprole, pyriprole, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluron, chlofluazuron, diflubenzuron, fluazuron, flucycloxuron, flufenoxuron, hexaflumuron, lufenuron, novaluron, noviflumuron, penfluron, teflubenzuron, triflumuron, buprofezin, cyromazine, diafenthiuron, azocyclotin, cyhexatin, fenbutatin-oxide, chlorfenapyr, binapacyrl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, *Bacillus thuringiensis* strains, spirodiclofen, spiromesifen, spirotetramat, 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS reg. no.: 382608-10-8), flonicamid, amitraz, propargite, thiocyclam hydrogen oxalate, thiosultap-sodium, azadirachtin, *Bacillus* spec., *Beauveria* spec., codlemone, *Metarrhizium* spec., *Paecilomyces* spec., thuringiensin, *Verticillium* spec., aluminium phosphid, methylbromide, sulfurylfluorid, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, and verbutin.

Compositions according to the invention may contain more than one active substance, such as, for example, the combination of beta-cyfluthrin and imidacloprid.

It is also possible to use active substance particles, or active-substance-containing particles and/or granules, which have been obtained for example via spray drying, spray solidification, or fluidized-bed processes (for example as described in EP 1 324 661, the entire disclosure of which is hereby incorporated by reference). These particles are usually coarsely particulate, for example, with a mean particle size d50 greater than 5 μm (determined after dispersion in the water phase by means of laser diffraction).

Polymer Dispersions.

The compositions of the invention also contain an aqueous polymer dispersion. Any polymer dispersion capable of reducing the environmental degradation and/or wash-off of the active substance(s) may be used. In particular, suitable polymers and polymer dispersions are described in detail in U.S. Provisional Patent Application No. 61/172,265 and PCT Application WO 2009/141109, the entire disclosures, including the portions which relate to polymers and polymer dispersion, are incorporated herein by reference. The dispersion may be an aqueous anionic, cationic, or amphoteric polymer dispersion and may include water, at least one polymer, and a dispersant. Suitable polymer dispersions are robust, stable, and compatible with active substances. In addition, the polymer dispersions may have a low toxicity and result in easy cleaning of equipment.

Suitable polymer dispersions may include finely particulate polymer dispersions which, at a concentration of about 0.025 wt % based on the solids content in demineralized water, has an absorbance, measured in a 1 cm cell at 535 nm, of less than about 2.0, such as less than about 1.0, or less than about 0.1.

Such polymer dispersions may include those which, after drying, have a glass transition temperature of from about 0° C. to about 120° C., such as from about 25° C. to about 90° C., from about 40° C. to about 80° C., or from about 45° C. to 55° C.

The glass transition temperature of the polymers is determined as follows. Polymer dispersion which had been left to dry in a DSC pan (drying for 24 hours at room temperature and 0% relative humidity) was determined using the Perkin-Elmer DSC-7 differential scanning calorimeter, equipped with intracooler, over three heating/cooling cycles (−100° C. to +150° C., heating rate 20 K/min, cooling rate 320 K/min, nitrogen flushing with a gas flow rate of 30 ml/min). The glass transition temperature was evaluated at half the level of the glass transition.

MFT may be determined using the THERMOSTAIR® temperature gradient testing apparatus (Coesfeld Messtechnik GmbH) as specified in DIN ISO 2115.

To determine the stability to electrolytes of the polymer dispersions, the absorption measurement may be carried out as above in parallel after dilution in water and in a $CaCl_2$ dispersion (50 mM). The measurement was carried out 24 hours after preparing the dilution. The relative difference of the two absorption values (water to $CaCl_2$ solution) is a measure for the stability to electrolytes. Polymer dispersions with good stability to electrolytes have a relative absorption difference of about 20% or less, such as about 5% or less, or about 3% or less.

Preferred polymer dispersions include those that are obtainable by polymerization of a monomer mixture containing one or more compounds selected from styrene, substituted styrene, acrylonitrile, methacrylonitrile, acrylic ester, and (meth)acrylamide.

Exemplary substituted styrenes include a-methylstyrene, vinyltoluene, or mixtures of these.

Exemplary acrylic esters include methyl acrylate, methyl methacrylate, ethyl acrylate, ethyl methacrylate, propyl acrylate, propyl acrylate, propyl methacrylate, n-butyl acrylate, iso-butyl acrylate, tert-butyl acrylate, n-butyl methacrylate, iso-butyl methacrylate, tert-butyl methacrylate, hexyl acrylate, hexyl methacrylate, ethylhexyl acrylate, stearyl acrylate, and stearyl methacrylate and mixtures thereof. In particular, mixtures of isomeric butyl acrylates may be employed.

Polymer dispersions may include those that are obtainable by polymerization of a monomer mixture containing an optionally substituted styrene and a $C_1$-$C_4$-alkyl(meth)acrylic ester.

Any suitable polymerization process may be used to form the polymer dispersions. For example, suitable cationic, aqueous polymer dispersions may be obtained by polymerization of a monomer mixture optionally (1) in the presence of an emulsifier (i.e. a second aqueous polymer dispersion) and/or optionally (2) in the presence of a hydrocolloid.

Monomer Mixture: In embodiments, the monomer mixture may comprise, consist essentially of, or consist of:
a) from about 20 to about 60 wt % of at least one optionally substituted styrene,
b) from about 40 to about 80 wt % of at least one $C_1$-$C_{18}$-(meth)acrylic ester and
c) from about 0 to about 20 wt %, such as from about 1 to about 10 wt %, of at least one nonionic ethylenically unsaturated monomer other than a) and b),
with the total of a)+b)+c) being 100 wt %.

Suitable monomers for group a) include styrene and/or substituted styrenes such as, for example, α-methylstyrene or vinyltoluene. It is especially preferred to employ unsubstituted styrene.

Suitable monomers of group b) include at least one $C_1$-$C_{18}$-(meth)acrylic acid ester. It is preferred to employ methacrylate, methyl methacrylate, ethyl acrylate, ethyl methacrylate, propyl acrylate, propyl methacrylate, n-, iso- and tert-butyl acrylate, n-, iso- and tert-butyl methacrylate, hexyl acrylate, hexyl methacrylate, ethylhexyl acrylate, stearyl acrylate and stearyl methacrylate. It is especially preferred to employ n-butyl acrylate or binary mixtures which contain from about 10 to about 90 wt % of n-butyl acrylate. It is very especially preferred to employ mixtures of n-butyl acrylate and tert-butyl acrylate.

Suitable monomers of group c) include at least one nonionic, ethylenically unsaturated monomer other than a) and b). It is preferred to employ nitriles such as, for example, acrylonitrile or methacrylonitrile, amides such as, for example, acrylamide, methacrylamide or N-methylolacrylamide, vinyl compounds such as, for example, vinyl acetate or vinyl propionate, dienes such as, for example, butadiene or isoprene, and esters of acrylic acid or methacrylic acid and at least one ethylene oxide unit such as, for example, hydroxyethyl methacrylate or diethylene glycol monomethacrylate.

A preferred polymer is a terpolymer of from about 40 to about 60 wt % styrene, about 20 to about 30 wt % n-butylacrylate, and about 20 to about 30 wt % t-butylacrylate.

Polymerization With An Emulsifier: An emulsifier may be obtained by a solution polymerization, preferably in a saturated $C_1$-$C_6$-carboxylic acid, of a monomer mixture comprising, consisting essentially of, or consisting of:

d) from about 15 to about 35 wt %, such as from about 20 to about 30 wt %, of at least one (meth)acrylic ester and/or (meth)acrylamide which contains a tertiary amino group, e) from about 65 to about 85 wt %, such as from about 70 to about 80 wt %, of at least one optionally substituted styrene and f) from about 0 to about 20 wt %, such as from about 0 to about 10 wt % or from about 1 to about 7 wt %, of a nonionic or cationic ethylenically unsaturated monomer other than d) and e), with the total of d)+e)+f) being 100 wt %.

The cationic polymer dispersion may be prepared by emulsion polymerization of a monomer mixture a) to c) in the presence of the emulsifier. The emulsifier, in turn, is prepared by solution polymerization of the monomer mixture d) to f) which can be carried out in a saturated $C_1$-$C_6$ carboxylic acid and which, if appropriate, is treated with water after an intermediate isolation and/or work-up.

To prepare the emulsifier, it is preferred to employ, as monomers of group d), (meth)acrylic esters or (meth)acrylamides of the formula (III)

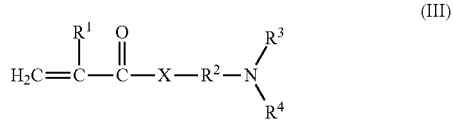

(III)

in which $R^1$ represents H or methyl, $R^2$ represents a linear $C_1$-$C_4$-alkylene radical, $R^3$ and $R^4$ are identical or different and represent $C_1$-$C_4$-alkyl and X represents O or NH.

The monomers of group d) which are employed in particular include compounds which correspond to the formula (III), where $R^3$ and $R^4$ are identical and represent methyl or ethyl. Monomers of group d) which are especially preferred are compounds of the formula (III) where X represents NH and $R^3$ and $R^4$ are identical and represent methyl or ethyl. Monomers of group d) which are also preferably employed are those which correspond to the formula (III) where $R^1$ represents H or methyl, $R^2$ represents n-propyl, $R^3$ and $R^4$ are identical and represent methyl and X represents NH.

To prepare the emulsifier, at least one styrene which may optionally be substituted is employed as monomer of group e). From the series of the substituted styrenes, it is preferred to employ α-methylstyrene or vinyltoluene. Unsubstituted styrene is especially preferably employed.

To prepare the emulsifier, the monomers of group f) which are employed are nonionic or cationic, ethylenically unsaturated monomers which are different from d) and e). It is preferred to employ nitriles such as, for example, acrylonitrile or methacrylonitrile, amides such as, for example, acrylamide, methacrylamide or N-methylolacrylamide, vinyl compounds such as, for example, vinyl acetate or vinyl propionate, acrylic acid or methacrylic acid esters of alcohols having 1-18 C atoms such as, for example, methyl acrylate, methyl methacrylate, ethyl acrylate, ethyl methacrylate, propyl acrylate, propyl methacrylate, n-, iso- and tert-butyl acrylate, n-, iso- and tert-butyl methacrylate, hexyl acrylate, hexyl methacrylate, ethylhexyl acrylate, stearyl acrylate and stearyl methacrylate or esters of acrylic acid or methacrylic acid which have been prepared by reaction with at least one ethylene oxide unit, such as, for example hydroxyethyl methacrylate or diethylene glycol monomethacrylate. It is especially preferred to employ, as cationic monomers of group f), vinylpyridine or the quaternized ammonium salts derived from formula (III), which may be obtained for example by reacting compounds of the formula (III) with customary quaternization reagents such as, for example, methyl chloride, benzyl chloride, dimethyl sulphate or epichlorohydrin, such as, for example, 2-(acryloyloxy)ethyltrimethylammonium chloride, 2-(methacryloyloxy)ethyltrimethyl-ammoniumchloride, 3-(acrylamido)propyltrimethylammonium chloride or 3-(methylacryl-amido)propyltrimethylammonium chloride.

The solution polymerization that may be carried out for preparing the emulsifier may be carried out as a free-radical polymerization in the presence of a solvent. Suitable solvents may include, for example, saturated $C_1$-$C_6$-carboxylic acids such as saturated $C_1$-$C_6$-monocarboxylic acids, and saturated $C_1$-$C_6$-dicarboxylic acids. The saturated $C_1$-$C_6$-carboxylic acids which are employed optionally have attached to them further substituents such as, for example, hydroxyl groups. The solution polymerization is preferably carried out in formic acid, acetic acid, propionic acid, butyric acid, isobutyric acid, valeric acid, isovaleric acid, caproic acid, hydroxypropionic acid or hydroxybutyric acid. Mixtures of a variety of saturated $C_1$-$C_6$-carboxylic acids may also be employed. It is preferred to carry out the solution polymerization in formic acid, acetic acid, propionic acid or hydroxypropionic acid, especially preferably in acetic acid. In this context, the saturated $C_1$-$C_6$-carboxylic acid employed preferably contains no more than about 20 wt % of water, such as no more than about 10 wt % of water, or no more than about 1 wt % of water, based on the total amount of solvent. It is very especially preferred to carry out the solution polymerization in at least about 99% strength acetic acid without the admixture of other carboxylic acids. The amount of solvent is chosen such that the concentration of the resulting emulsifier solution is from about 20 to about 70 wt %, calculated from the amount of monomers employed.

The solution polymerization is preferably carried out in the presence of a polymerization regulator. Suitable polymerization regulators are, mainly, sulphur compounds such as, for example, thioglycolic acid or mercaptans such as, for example, ethylmercaptan, n-butylmercaptan, tert-butylmercaptan, n-dodecylmercaptan or tert-dodecylmercaptan. It is preferred to employ mercaptans, especially preferably $C_8$-$C_{14}$-alkylmercaptans.

The solution polymerization may be initiated by a free-radical initiator. Free-radical initiators for the solution polymerization which are preferably employed include peroxo- or azo- compounds such as, for example, hydrogen peroxide, sodium peroxodisulphate, potassium peroxodisulphate and ammonium peroxodisulphate, di-tert-butyl peroxide, dibenzoyl peroxide, azobisisobutyronitrile, 2,2'-azobis(2-methylbutyronitrile), 2,2'-azobis(2,4-dimethyl-valeronitrile) or 2,2'- azobis(2-amidinopropane) dihydrochloride. It is preferred to employ azo compounds, especially preferably nitriles such as, for example azobisisobutyronitrile, 2,2'-azobis(2-methylbutyronitrile) or 2,2'-azobis(2,4-dimethylvaleronitrile).

When carrying out the solution polymerization, the amount of free-radical initiator and polymerization regulator is preferably chosen such that an emulsifier with a weight-average molar weight of from about 5,000 to about 100,000 g/mol, such as from about 15,000 to about 75,000, or from about 25,000 to about 50,000 is obtained. The determination of the molecular weight distribution and of the weight-average molar weight may be carried out by methods known to the skilled worker such as, for example, gel permeation chromatography, light scattering or ultracentrifugation.

After the solution polymerization has ended, the emulsifier obtained is either isolated by intermediate isolation or directly treated with water. It is preferred to treat the emulsifier obtained directly with water and to prepare, by stirring, a homogeneous liquid phase in which the emulsifier is present in partially dissolved and partially dispersed form. The concentration of the emulsifier in the liquid phase after the addition of water is from about 2 to about 20 wt %, such as from about 5 to about 15 wt %. This liquid phase may be employed directly for carrying out the emulsion polymerization for the preparation of the cationic aqueous polymer dispersion.

Next, the cationic aqueous polymer dispersion is prepared by emulsion polymerization of a monomer mixture, as described above, with the emulsifier.

Polymerization With A Hydrocolloid: In another embodiment, suitable aqueous polymer dispersions may be obtained by polymerization of a monomer mixture in the presence of a hydrocolloid as the main chain to form a grafted polymer.

Hydrocolloids are macromolecular, hydrophilic substances which are soluble or dispersible in water and swellable, giving rise to viscous solutions, gels or stabilized systems, such as, for example, agar, carrageenan, xanthan, gellan, galactomannans, gum arabic, tragacanth, karaya, curdlan, beta-glucan, alginates, mannans, chitosan, celluloses, proteins, gelatin, pectin, starch (and their modified and/or degraded (for example hydrolyzed and/or oxidized) forms), and synthetic water-soluble polymers. An oxidized starch may be made by treating a starch with an aqueous oxidizing agent such as hydrogen peroxide, sodium hypochlorite, hypochlorous acid, or ammonium persulfate. Under such conditions, the oxidizing agent reacts with the starch to cleave the polymeric chains and to oxidize the end groups from aldehyde to carboxylic acid groups. The hydrocolloid may be, for example, degraded starch with a molar weight $M_n$ of, for example, 500 to 10,000. An exemplary degraded starch that may be used is PERFECTAMYL® 4692 (commercially available from Avebe).

Such grafted aqueous polymer dispersions may be obtained for example by radical-initiated emulsion copolymerization of ethylenically unsaturated monomers in the presence of a hydrocolloid, such as a starch, wherein the ethylenically unsaturated monomers employed comprises, consists essentially of, or consists of:
 (a) from about 30 to about 60 wt % of at least one optionally substituted styrene,
 (b) from about 60 to about 30 wt % of at least one $C_1$-$C_4$-alkyl (meth)acrylate,
 (c) from about 0 to about 10 wt %, such as from about 1 to about 7 wt %, of other ethylenically unsaturated copolymerizable monomers; and
 (d) from about 5 to about 40 wt %, such as from about 5 to about 10 wt % or from about 10 to about 30 wt %, of degraded starch, with the total of (a)+(b)+(c)+(d) being 100%. The free-radical-initiator employed for the radical-initiated emulsion polymerization may be a graft-active, water-soluble redox system. Suitable and preferred monomers a), b), and c) include the compounds described previously for the cationic polymer dispersion.

The grafted polymer dispersions generally have a particle size below about 100 nm, such as from about 50 to about 90 nm, or from about 30 to about 60 nm. In embodiments, the particles have a polymer core with a starch shell. The starch shell may be from about 2 to about 15 nm in thickness, such as from about 3 to about 10 nm, or from about 4 to about 6 nm; and the core may be from about 40 to about 60 nm.

The polymer in the polymer dispersion may have a molecular weight of greater than or equal to about 50,000 D, such as from about 50,000 D to about 100,000 D. Of this, there is no relevant contributions of oligomers (moieties of less than 1000 D).

In embodiments, the concentration of polymer in the aqueous polymer dispersion may be any suitable amount, such as from about 10 to about 40 wt %, from about 15 to about 35 wt %, from about 15 to about 20 wt %, or from about 20 to about 30 wt %, based on the weight of the polymer dispersion. Of this polymer, the concentration of component a) based on the weight of the polymer dispersion may be from about 5 to about 20 wt %, such as from about 7 to about 15 wt %, or from about 9 to about 12 wt %. The concentration of component b) based on the weight of the polymer dispersion may be from about 3 to about 20 wt %, such as from about 8 to about 17 wt %, or from about 10 to about 13 wt %.

In another embodiment, the aqueous polymer dispersion includes styrene in an amount of from about 5 to about 15 wt %, such as from about 8 to about 12 wt %; n-buytlacrylate in an amount of from about 1 to about 10 wt %, such as from about 3 to about 7 wt %; t-butylacrylate in an amount of from about 1 to about 10 wt %, such as from about 3 to about 7 wt %; and oxidized starch in an amount of from about 3 to about 10 wt %, such as from about 5 to about 8 wt %.

An exemplary commercially available polymer dispersion that may be used in embodiments includes POLYGRAPHIX® (commercially available from Kemira Chemicals, Inc.).

The viscosity of, for example, a 20% polymer aqueous polymer dispersion is generally, from about 3 to about 30 mPas, measured at a temperature of about 23° C. The mean particle size of a 20% dispersion is less than about 100 nm, such as from about 5 to about 50 nm. The mean particle size may be determined by methods known to the skilled worker such as, for example, laser correlation spectroscopy, ultracentrifugation or turbidimetry.

Dispersants: The polymer dispersions according to the invention may include nonionic and/or ionic dispersants.

Exemplary nonionic dispersants include polyethylene oxide/polypropylene oxide block copolymers, polyethylene glycol ethers of linear alcohols, reaction products of fatty acids with ethylene oxide and/or propylene oxide, furthermore polyvinyl alcohol, polyvinylpyrrolidone, mixed polymers of polyvinyl alcohol and polyvinylpyrrolidone, and copolymers of (meth)acrylic acid, (meth)acrylic esters, furthermore alkyl ethoxylates, and alkylaryl ethoxylates, which may optionally be phosphated and optionally be neutralized with bases (e.g. sorbitol ethoxylates).

Exemplary ionic dispersants include anionic dispersants, for example modified sodium lignosulphonates, Kraft sodium lignosulphonates, naphthalene-formaldehyde condensates, polyaspartic acid, polyacrylates, polyethylene sulphonates, modified starch, gelatin, gelatin derivatives or anionic surfactants (such as, for example, aromatic or aliphatic sulphates and sulphonates, or sulphated or sulphonated aromatic or aliphatic ethoxylates).

When using finely distributed active substance particles or active-substance-containing carrier particles, it is preferred to use anionic and/or nonionic dispersants.

Optional Additives

Besides the above-mentioned components, the compositions may optionally contain one or more of a thickener (optionally including thickening activator), a preservative, an antifoam, one or more acids or bases in such an amount as to adjust the pH of the mixture in a targeted manner, or to activate thickener, and further components for optimizing the use properties of the formulation.

Thickeners: Suitable thickeners include synthetic and biological substances that act as thickeners and may conventionally be employed for this purpose in agrochemical compositions. Exemplary thickeners include inorganic particles such as carbonates, silicates and oxides, and also organic substances such as urea/formaldehyde condensates; synthetic thickeners such as polyacrylate thickeners, for example, CARBOPOL® and PEMULEN® thickeners (commercially available from Lubrizol); biological thickeners such as xanthan gum, for example, KELZAN® S (commercially available from CP Kelco), RHODICARE T®, and RHODOPOL 23® (both commercially available from Rhodia); and inorganic thickeners such as layer silicates, for example kaolin, montmorillonite, and laoponite. Other examples include rutile, silicon dioxide, what is known as highly disperse silica, silica gels, and also natural and synthetic silicates and talc. The thickeners may be present in any suitable amount, for example, from about 0.01 to about 0.5 wt % based on the total pesticide composition, such as from about 0.07 to about 0.30, or about 0.25.

Preservatives: Suitable preservatives include substances that may be employed for this purpose in agrochemical compositions. Exemplary preservatives include citric acid monohydrate, isothiazolinones, 1,2-benzisothiazolon-3-one. Specific examples include PREVENTOL® (commercially available from Lanxess AG) and PROXEL® (commercially available from Arch UK Biocides, Ltd.). The preservatives may be present in any suitable amount, for example, from about 0.01 to about 0.4 wt % based on the total pesticide composition, such as from about 0.1 to about 0.2, or from about 0.15 to about 0.18.

Antifoams: Although the polymer dispersions often exhibit little to no foaming behavior, suitable antifoams include substances may be employed for this purpose in agrochemical compositions. Exemplary antifoams include magnesium stearate, or silicone oils such as RHODORSIL ANTIFOAM 416® (commercially available from Rhodia). The antifoams may be present in any suitable amount, for example, from about 0.01 to about 0.3 wt % based on total pesticide composition, such as from about 0.1 to about 0.2, or about 0.15.

In addition, propylene glycol may also be added to the polymer suspension.

Composition Preparation

The pesticidal compositions of the invention may be prepared by any suitable method. In such methods, the components of the pesticidal composition are mixed with one another in the ratios desired in each case. In mixing the components, the polymer dispersion may be added to the active substance or the active substance may be added to the polymer dispersion. In some embodiments, the thickener may be added last.

The solid components are expediently employed in a finely-ground state (e.g. <5 μm. However, it is also possible to subject the suspension obtained after mixing the components first to coarse milling and then to fine milling, so that the main particle size is, for example, about 5 μm or less.

When forming the pesticidal compositions, the mixing temperatures may be varied within a certain range. Suitable temperatures may be from about 10° C. to about 60° C., such as from about 15° C. to about 40° C. Customary mixing and grinding equipment which is employed for the preparation of agrochemical formulations is suitable for carrying out the process according to the invention.

In concentrated formulations, the amounts of active substance and polymer in the compositions may be present in any effective amount and varied within a wide range. For example, the active substance may be present in any amount from about 0.01 to about 40 wt % based on the total pesticide composition, such as from about 0.1 to about 20 wt %, about 1 to about 20 wt %, or about 2 to about 10 wt %. For example, in a 50.0 g/l concentrate of active substance, the active substance may be present in an amount of from about 3 to about 7 wt %, such as from about 4 to about 6 wt %, or about 5 wt %.

In such concentrated formulations, the polymer may be present in any amount from about 1 to about 50 wt % based on the total pesticide composition, such as from about 2 to about 40 wt %, from about 6 to about 20 wt %, from about 10 to about 13 wt %, or from about 11 to about 12 wt %. In this context, the polymer amounts specified indicate the content based on the polymer solids content. Frequently, it is in the form of an aqueous dispersion that the polymers are synthesized, or offered for sale, and employed for preparing the compositions according to the invention.

In concentrated formulations, the ratio of active substance to polymer may be from about 1:1 to about 1:4, such as about 1:3 or about 1:2. Because this is a ratio of active substance to polymer, the amount of polymer dispersion to be added depends on the concentration of polymer in the polymer dispersion. For example, if the desired ratio of active substance to polymer is 1:2, if POLYGRAPHIX® was to be used as the polymer dispersion, and if the composition was to include 6 wt % deltamethrin, then about 50 wt % of POLYGRAPHIX® (a 240 g/l concentrate itself) would be added so that the polymer would be present at about 12 wt % [0.24×50=0.12]. In another example, if a 4.708 wt % deltamethrin concentrate was desired, 39.234 wt % POLYGRAPHIX® (9.416 wt % polymer) would be needed to yield the desired concentrate with the same 1:2 ratio. Depending on the desired concentration of active ingredient, the water content and/or other optional ingredients may be increased or decreased.

In ready-to-use formulations (as well as when concentrated formulations are diluted), the amount of active substance may be varied within a wide range, such as from about 0.001 to about 0.5 wt % based on the total pesticide composition, or about 0.01 to about 0.1 wt %. The amount of polymer is generally present in an amount of from about 0.002 to about 1 wt % based on the total pesticide composition, such as from about 0.004 to about 0.8 wt %, or about 0.01 to about 0.4 wt %. As with concentrated formulations, the amounts specified indicate the content based on the solids content.

In addition, the aqueous polymer dispersion may be supplied separately as a weather-resistance additive to be added to pesticidal compositions, or it may be supplied in powder form to be added with or without water to other pesticidal compositions, thereby extending the weather resistance of any suitable pesticidal composition. In addition, the polymer dispersion may be sprayed over the top of already applied pesticidal compositions to impart weather resistance.

Application of the Composition

If the compositions are in ready-to use form, no dilution is necessary. However, concentrated compositions may be diluted in water for their intended use. In this context, the compositions are diluted to such an extent that the active substance content, with the intended application rate, ensures sufficient active substance activity. For example, the dilution may yield compositions that correspond to the above-specified ready-to-use compositions.

The ready-to-use or diluted solutions may be applied in any customary manner, for example by spraying with hand-operated or electrical sprayers, brushing, misting, painting, etc. The active substance and the polymer dispersion may be mixed together and then applied as a mixture, or applied separately. For example, the active substance may be applied, followed by application of the polymer suspension; the polymer suspension may be applied first, followed by application of the active substance and a second optional application of the polymer suspension thereon; or the mixture of the polymer suspension and active substance may be applied, either preceded by and/or followed by the application of the polymer suspension.

In the context of spraying, the active substance may be generally applied at an application rate of from about 1 to about 1000 mg/m$^2$, such as from about 1 to about 500 mg/m$^2$, from about 5 to about 250 mg/m$^2$, or from about 10 to about 250 mg/m$^2$.

The compositions according to the invention may be applied at such a dilution rate and application rate to a surface that the polymer is applied at a deposition rate (based on solid) of from about 1.0 mg/m$^2$ to about 2000 mg/m$^2$, such as from about 5.0 mg/m$^2$ to about 500 mg/m$^2$, from about 5 mg/m$^2$ to about 200 mg/m$^2$, or from about 10 mg/m$^2$ to about 200 mg/m$^2$.

The compositions according to the invention may be applied to any surface which has a need to be protected from pests, such as inside buildings or in the open, for example wallpaper, concrete, render, ashlar, timber (treated and untreated), ceramic (glazed and unglazed), straw or thatch, brick (untreated, limewashed, painted), clay minerals (for example terracotta), chalky, limy, gypsiferous, cement-containing and loamy surfaces.

In particular, the compositions may be applied to outdoor surfaces that may be exposed to water from naturally or artificially occurring sources, such as, rain, snow, flooding, sprinkler systems, irrigation, etc. The compositions after application have an unexpectedly high adhesion to surfaces, even when exposed to water. Because the compositions are aqueous, this desirable property is even more surprising. Also, the efficacy of the compositions is improved over the efficacy of an insecticidal composition that does not include the polymer dispersion.

The adhesion (or fastness) of the compositions to the various surfaces may be quantified in terms of percent wash-off when exposed to an amount of water over a period of time. The percent wash-off is the amount of active substance that is washed off when the treated surface is exposed to a controlled amount of water, such as simulated rain.

The percent wash-off varies according to the surface material. For example, porosity, surface texture, and/or microstructure may contribute to the percent wash-off. For example, when applied to smooth surfaces (i.e. glazed ceramic tiles), the compositions may have a percent wash-off of from about 50% or less, such as from about 45% to about 5%, from about 30% to about 12%, from about 25% to about 12%, from about 25% to about 16%, or from about 16% to about 12%, when exposed to about 1 inch/hour or less of rainfall for 1 hour. When applied to rougher surfaces (i.e. concrete, bricks, etc.), the compositions may have a percent wash-off of from about 25% or less, such as from about 25% to about 2%, from about 24% to about 4%, from about 14% to about 5%, from about 14% to about 6%, or from about 6% to about 4%, when exposed to about 1 inch/hour or less of rainfall for 1 hour.

The adhesion (or fastness) may also be quantified by comparing a composition according to the present invention, which includes an active substance and a polymer dispersion, with a comparative composition that does not include the polymer dispersion, but has the same active ingredient concentration (the balance thereof being made up by water). The % reduction in the amount of wash-off realized by the composition of the present invention from such a comparative composition is at least about a 10% reduction, such as from about 10 to about 90%, such as from about 25 to about 80%, from about 60 to about 75%, or from about 62 to about 72%.

The following examples are illustrative only and are not intended to limit the disclosure in any way.

EXAMPLE 1

Polymer Dispersion Preparation

In a flask equipped with stirrer, reflux condenser, and heating jacket, 124.5 g of oxidatively degraded potato starch were dispersed under nitrogen in 985 g of deionized water and dissolved by warming. In succession, 42.7 g of a 1% strength iron(II) sulphate solution and 116 g of a 3% strength hydrogen peroxide solution were added, and the mixture was stirred for 15 min at 86° C. After 15 minutes, the following two metering solutions were metered in simultaneously, but separately with constant dosing rate within 90 min at 86° C.:

1) 321 g of a mixture of styrene, n-butyl acrylate, and tert-butyl acrylate
2) 93.7 g of a 3% strength hydrogen peroxide solution.

After all of the solutions were metered in, stirring was continued for 15 min at 86° C., and 2 g of t-butyl hydroperoxide were then added to let the mixture after-react. After a further 60 min at 86° C., the mixture was cooled to room temperature, 10 g of a 10% strength solution of EDTA in the form of the tetrasodium salt were added, and a pH of 6.5 was adjusted with 13 g of a 10% strength sodium hydroxide solution. The mixture was passed through a 100 μm filter cloth, giving a finely divided dispersion with a solids content of 24.0% by weight.

The ratio between styrene, n-butyl acrylate and tert-butyl acrylate can be varied, depending on the desired polymer properties (glass transition temperature, minimum film-forming temperature). The suitable ratio can be determined experimentally following the above protocol.

EXAMPLE 2

Suspension A Preparation

A polymer dispersion (hereinbelow referred to as PD-SACP) was prepared in accordance with the above Example 1. 5.88 wt % of deltamethrin was mixed with 49.04 wt % of PD-SACP. The balance of the suspension was made up with water and various inert ingredients, such as preservatives, thickeners, antifoams, other ingredients to form Suspension A. See Table 1 below.

EXAMPLE 3

Suspension B Preparation

A comparative suspension of SUSPEND® SC (commercially available from Bayer Environmental Science) was used as Suspension B. SUSPEND SC includes 4.75 wt % deltamethrin and 95.25 wt % water and inert ingredients. See Table 1 below.

TABLE 1

Suspension Formulations

| Component | Suspension A (wt %) | Suspension B (wt %) |
|---|---|---|
| Deltamethrin | 5.88 | 4.75 |
| PD-SACP | 49.04 | — |
| Inert ingredients | 56.84 | 95.25 |

EXAMPLE 4

Percent Wash-Off Test—Comparison of Suspension A with Comparative Suspension B. The below study was designed to test the difference in rain fastness between Suspensions A and B.

A. Dilutions. Suspensions A and B were tested with a 0.05% (w/w) solution and 2.5 mg A.I./ft$^2$ which was slightly greater than the maximum label rate for Suspend® SC (the maximum label rate is 0.06% and 1 gallon/1000 ft$^2$, which equals 2.27 mg A.I./ft$^2$). The detailed dilution of each suspension and application information is provided in Table 2 (below):

TABLE 2

Dilutions

| Formulation | Active Ingredient | Dilution of product to make 250 mL spray solution | spray amount per ft$^2$ | AI per ft$^2$ |
|---|---|---|---|---|
| Suspension A | Deltamethrin | 2.5 ml | 5 ml | 2.5 mg |
| Suspension B | Deltamethrin | 2 ml | 5 ml | 2.5 mg |

The spray solutions were prepared with tap water in a 500-mL amber glass bottle. The sprayer was a plastic mist sprayer with a glass insert to eliminate the potential absorption on the bottle and sprayer. Each spray solution was prepared immediately before application.

B. Test Building Materials. Two types of building material were used in the studies: glazed ceramic tile and concrete slab:

(1) Glazed ceramic tile: commercially available 12"×12" glazed ceramic floor tile was purchased from HomeDepot® (Model number: RGN22WT, SKU number: 177439); and (2) Concrete slab: 12"×12" concrete slab was made indoors two weeks before the test by using the concrete mix purchased from HomeDepot® (Model number: 110180, SKU number: 169765). The surface of the concrete was relatively smooth, similar to the surface of building foundations.

Glazed ceramic tiles were used as a test material because its smoothness, low porosity, and inert surface should represent a worst-case for wash-off. The tiles were prepared by washing them with hot tap water to remove surface dust and any potential chemical residues, and dried for 24 hours before application.

Concrete slabs were used as a second test material because concrete is widely used in the lower portion of vertical walls (below the siding) in buildings, as well as for sidewalks and driveways. The concrete slabs were prepared by soaking them in tap water in a plastic container for three days and washing them with a brush to remove dust and alkali material on the surface. The concrete slab was dried for three days before application.

C. Rainfall Simulator. The rainfall simulator was made with a FullJet stainless steel spray nozzle (model number: FL-10VS). It is a large droplet wide angle full cone nozzle. The rainfall intensity was controlled by controlling the pressure with an inlet regulator. The nozzle was placed on the top center of a 3 ft×3 ft wood frame with plastic file as walls. The nozzle was about 6 ft above the center of the test material.

The target rainfall intensity used in this study was 1 in/hr, the duration for the test was 1 hour. This intensity has been widely used in runoff and wash-off tests, including an earlier wash-off study with pyrethroids. See Harbourt et al., *Washoff/Runoff Of Cypermethrin Residues From Slabs Of External Building Material Surfaces Using Simulated Runoff*; Waterborne Environmental Report Number 794.10. (2009). In many places in the U.S., several storms with this intensity or greater may be expected each year. In California, an area of major use for this product, this rainfall intensity was close to the 10-year 1-hour rainfall frequency. See U.S. Department of Commerce, Technical Paper No. 40, *Rainfall Frequency Atlas of the United States for Durations from 30 Minutes to 24 Hours and Return Periods from 1 to 100 years*, Washington, D.C. (May 1961).

The rainfall intensity was calibrated by collecting the rainfall through the surface of the test material in one hour.

D. Application of the Spray Solutions. The edges of the test tile or slab were taped with half inch wide paper tape since the edge was glued on the test material stand during the wash-off. The individual test material was put on a scale before the application, the spray solution was evenly sprayed on the surface, and the application amount was read from the scale by assuming the density of the spray solution is 1 g/mL. After application, the test tile or slab was dried for 24 hours before the wash-off. There were triplicate samples for each formulation on each type of test building material.

E. Wash-Off Test. Each individual tile or slab was put on the stainless steel stand and sealed with silicone sealant along the edge. The stand with sealed test material was moved to the center of rainfall simulator after about one hour. The test surface was 30 degree to the vertical (or 60 degree to the ground). The wash-off was then simulated with the rainfall intensity described above. The wash-off was collected in a 2.5-L amber glass jar. A 30 degree angle was chosen to make certain that the rain water flowed across the surface of the slab to maximize wash-off. The angle of 30 degrees is an arbitrary choice since the angle could vary from 0 to 90 degrees depending on the wind speed. However, this angle is consistent with an earlier pyrethroid wash-off study (see Harbourt et al., 2009).

F. Analytical Procedures. The samples were analyzed on a Shimadzu HPLC pumps coupled with an Applied Bioscience Sciex 4000 LC/MS/MS system. The method showed good linearity for deltamethrin from 0.0001 ppb to 1 ppb. Phenoxy $^{13}C_6$-deltamethrin was used as an internal standard.

G. Sample Types and Preparation.

Quality Control samples—Acetonitrile (ACN) spikes: To verify the concentration of spike solutions and the amount sprayed on the test material, similar amount of spray solutions were also sprayed to a 500-mL amber bottle containing 250 mL acetonitrile before and after each application on the triplicate test material samples. A small aliquot of ACN spikes was diluted with same volume of pure water to have 1:1 ACN/water sample before HPLC-MS/MS analysis.

Quality Control samples—Water spikes: To test the extraction efficiency and storage stability, similar amounts of spray solutions were also sprayed to a 2.5-L amber glass jar containing 1000 mL tap water. The pH of the water samples was adjusted to less than 4.0 using formic acid. The same amount of ACN was added to the jar, the jar was shaken for 30 minutes on shaker, resulting in a 1:1 ACN/water sample before HPLC-MS/MS analysis.

Tape sample: The tape on the edge of the test material during the application was immersed in the 100 mL acetonitrile after the application to quantify the amount which was sprayed on the tape during application. A small aliquot of ACN spikes was diluted with same volume of pure water to produce a 1:1 ACN/water sample before HPLC-MS/MS analysis.

Wash-off samples: Wash-off sample was adjusted to pH less than 4.0 immediately after each test with formic acid. The volume of the wash-off samples were calculated by the sample jar weight before and after the test by assuming the density of wash-off was one. The same amount of ACN was added to the jar, the jar was shaken for 30 minutes on shaker, resulting in a 1:1 ACN/water sample before HPLC-MS/MS analysis.

H. Results and Discussions.

Recoveries of quality control samples: The table below shows the recoveries from quality control spikes during the tile and concrete slab tests. The recoveries from ACN spikes ranged from 82.3% to 105% and the recoveries from water spikes ranged from 74.8% to 112% for the two formulations of deltamethrin (See Table 3). These recoveries validated the test and analytical procedures for this study.

TABLE 3

Quality Control Sample Recovery

| | | QC recovery, % | |
|---|---|---|---|
| Formulation | Spike Type | Spike samples during tile test | Spike samples during concrete slab test |
| Suspension B | Spike in ACN before application | 102 | 97.8 |
| | Spike in ACN after application | 105 | 105 |
| | Spike in water after application | 112 | 98.4 |
| Suspension A | Spike in ACN before application | 85.8 | 82.3 |
| | Spike in ACN after application | 82.8 | 83.5 |
| | Spike in water after application | 78.6 | 74.8 |

Improvement of rain fastness on test surfaces: The wash-off percentage of deltamethrin in Suspend SC 50 from tile during the one hour test with one inch simulated rainfall was 47.7% and was reduced to 17.8% for Suspension A according to the invention (Table 4).

TABLE 4

Wash-off Percentage of Different Formulations from Test Surfaces

| Formulation | Test Surface | Wash-off (%) | Average | STDEV |
|---|---|---|---|---|
| Suspension B | Tile | 47.5 | 47.7 | 1.3 |
| | | 49.1 | | |
| | | 46.6 | | |
| Suspension A | | 12.3 | 17.8 | 6.0 |
| | | 16.7 | | |
| | | 24.2 | | |
| Suspension B | Concrete Slab | 35.5 | 29.6 | 5.5 |
| | | 28.7 | | |
| | | 24.6 | | |
| Suspension A | | 14.6 | 8.4 | 5.4 |
| | | 5.7 | | |
| | | 4.9 | | |

The wash-off percentage on concrete slabs were lower than with glazed ceramic tile. The wash-off percentage of Suspend SC 50 was 29.6% and was reduced to 8.4% for Deltamethrin SC 62.5 (Table 5).

t-test procedure and result: t-test statistical procedure (two-sample assuming unequal variances) was used to compare the mean of wash-off percentage with Suspension B and Suspension A. The null hypothesis under evaluation is that the mean wash-off percent of applied mass was equal for both formulation types with the alternative hypothesis indicating that there is a statistical difference between mean wash-off percent of applied mass by formulation type. The procedures were completed for an alpha level of 0.05 or at the 95% confidence interval.

Results from t-test showed that the two-tail $p_{(0.05)}$ value were 0.0137 (t=4.303) and 0.0088 (t=2.776) for the tile and concrete slab, respectively, and thus indicate significant differences between formulations Suspension B and Suspension A on both tile and concrete slab (Table 5).

TABLE 5

Result of t-Test (Two-Sample Assuming Unequal Variances)

| | Tile | | Concrete Slab | |
|---|---|---|---|---|
| | Suspension B | Suspension A | Suspension B | Suspension A |
| Mean | 47.7333333 | 17.7333333 | 29.6 | 8.4 |
| Variance | 1.60333333 | 36.2033333 | 30.31 | 28.99 |
| Observations | 3 | 3 | 3 | 3 |
| Hypothesized Mean Difference | 0 | | 0 | |
| df | 2 | | 4 | |
| t Stat | 8.45079736 | | 4.76836116 | |
| P(T <= t) one-tail | 0.00685753 | | 0.00442535 | |
| t Critical one-tail | 2.91998558 | | 2.13184678 | |
| P(T <= t) two-tail | 0.01371506 | | 0.00885071 | |
| t Critical two-tail | 4.30265273 | | 2.77644511 | |

Thus, about 47.7% of the deltamethrin in Suspension B applied to tile washed off, compared to 17.8% wash-off with Suspension A. Probably due to its surface microstructure, the amount of wash-off on concrete slabs was less, specifically, about 29.6% of the deltamethrin in Suspension B washed off the concrete slabs, compared to the 8.4% wash-off for Suspension A. These results are especially surprising because suspension concentrate-type products are often susceptible to wash-off.

It will be appreciated that various combinations of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A pesticidal composition, comprising: a pesticide, and an aqueous polymer dispersion comprising a dispersion of a styrene/n-butyl acrylate/t-butyl acrylate terpolymer,
   wherein the pesticidal composition has at least a 10% reduction in the amount of wash-off compared to the same pesticidal composition without the aqueous polymer dispersion,
   and wherein the pesticidal composition has a percent wash-off of about 50% or less when exposed to 1 inch/hour of rainfall for 1 hour,
   and wherein the terpolymer is grafted onto an oxidized starch.

2. The pesticidal composition of claim 1, wherein the reduction in the amount of wash-off compared to the same pesticidal composition without the aqueous polymer dispersion is from about 60 to about 90%.

3. The pesticidal composition of claim 1, further comprising a nonionic and/or ionic dispersant.

4. The pesticidal composition of claim 1, wherein the aqueous polymer dispersion is a cationic polymer dispersion, which contains an emulsifier.

5. The pesticidal composition of claim 4, wherein the emulsifier comprises at least one (meth)acrylic ester or (meth) acrylamide, and wherein said at least one (meth)acrylic ester or (meth)acrylamide contains a tertiary amino group.

6. The pesticidal composition of claim 1, wherein the % weight ratio of pesticide to polymer is from about 1:1 to about 1:4.

7. The pesticidal composition of claim 1, wherein the percent wash-off is about 25% or less when applied to a glazed ceramic tile.

8. The pesticidal composition of claim 1, wherein the percent wash-off is about 14% or less when applied to concrete.

9. A method of treating a surface with a pesticidal composition, the method comprising:
   applying to an area to be treated the pesticidal composition of claim 1, and
   allowing the pesticidal composition to dry on the treated surface.

10. A method of treating a surface with a pesticidal composition according to claim 1, the method comprising:
    mixing an aqueous polymer dispersion with a pesticide to form the pesticidal composition, and
    applying to the surface the pesticidal composition,
    wherein the pesticidal composition has at least a 10% reduction in the amount of wash-off compared to the same a pesticidal composition without the aqueous polymer dispersion.

11. A process for preparing a composition according to claim 1, comprising mixing the pesticide with the polymer dispersion.

* * * * *